(12) United States Patent
Suzuki et al.

(10) Patent No.: US 11,858,074 B2
(45) Date of Patent: Jan. 2, 2024

(54) MEDICAL APPARATUS REMANUFACTURING METHOD

(71) Applicant: OLYMPUS CORPORATION, Hachioji (JP)

(72) Inventors: Tatsuya Suzuki, Hachioji (JP); Hideo Sanai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 396 days.

(21) Appl. No.: 17/078,162

(22) Filed: Oct. 23, 2020

(65) Prior Publication Data

US 2021/0053165 A1 Feb. 25, 2021

Related U.S. Application Data

(63) Continuation of application No. PCT/JP2018/025876, filed on Jul. 9, 2018.

(51) Int. Cl.
*A61B 17/00* (2006.01)
*A61B 17/32* (2006.01)
(Continued)

(52) U.S. Cl.
CPC .... *B23P 11/025* (2013.01); *A61B 17/320068* (2013.01); *A61B 18/14* (2013.01); *A61L 2/206* (2013.01); *A61L 2/208* (2013.01); *B23P 6/00* (2013.01); *A61B 2017/00526* (2013.01); *A61B 2017/320082* (2017.08); *A61B 2018/00607* (2013.01); *A61B 2018/00994* (2013.01);
(Continued)

(58) Field of Classification Search
CPC ...................... B23P 11/025; A61B 2090/0813
See application file for complete search history.

(56) References Cited

U.S. PATENT DOCUMENTS 3,416,823 A * 12/1968 Ulrich ................... F16B 39/284
411/908
3,724,059 A * 4/1973 Celovsky ................ B21B 28/02
29/426.6
(Continued)

FOREIGN PATENT DOCUMENTS

JP H08-28532 A 2/1996
JP H11-191678 A 7/1999
(Continued)

OTHER PUBLICATIONS

Aug. 21, 2018 International Search Report issued in International Patent Application No. PCT/JP2018/025876.
(Continued)

*Primary Examiner* — Jacob J Cigna
(74) *Attorney, Agent, or Firm* — Oliff PLC (57) ABSTRACT

A medical apparatus remanufacturing method includes: disassembling a housing including a first housing and a second housing. The first housing can include a boss that is press-fitted to a boss hole of a press-fitted portion of a second housing to form an assembled state in which the first housing and the second housing are assembled to each other. The housing is disassembled by changing a temperature of at least one of the boss or the press-fitted portion to decrease a contact surface pressure between the boss and the boss hole, and removing the boss from the boss hole to release the assembled state.

19 Claims, 10 Drawing Sheets

(51) Int. Cl.
  *A61B 18/00* (2006.01)
  *A61B 18/14* (2006.01)
  *B23P 11/02* (2006.01)
  *B23P 6/00* (2006.01)
  *A61L 2/20* (2006.01)
  *A61B 90/00* (2016.01)
  *A61L 101/02* (2006.01)
  *A61L 101/44* (2006.01)

(52) U.S. Cl.
  CPC ... *A61B 2090/0813* (2016.02); *A61L 2101/02* (2020.08); *A61L 2101/44* (2020.08); *A61L 2202/24* (2013.01)

(56) References Cited

U.S. PATENT DOCUMENTS

| | | | | |
|---|---|---|---|---|
| 3,783,429 | A * | 1/1974 | Otte | H01R 13/052 411/909 |
| 5,245,738 | A * | 9/1993 | Johnson | F16B 31/007 29/447 |
| 7,770,278 | B2 * | 8/2010 | Davies | F16B 4/006 29/447 |
| 8,764,424 | B2 * | 7/2014 | Kirkland | F04C 2/16 418/179 |
| 9,360,029 | B2 * | 6/2016 | Wallace | F16D 1/0858 |
| 9,700,339 | B2 * | 7/2017 | Nield | A61N 7/00 |
| 11,376,040 | B2 * | 7/2022 | Kalina, Jr. | A61F 9/007 |
| 2003/0170092 | A1 * | 9/2003 | Chiodo | C22F 1/006 411/82.5 |
| 2004/0187287 | A1 * | 9/2004 | Davies | B23P 11/025 29/447 |
| 2007/0159204 | A1 | 7/2007 | Hara et al. | |
| 2010/0044417 | A1 | 2/2010 | Bruck et al. | |
| 2010/0298743 | A1 * | 11/2010 | Nield | A61B 17/320068 606/1 |
| 2012/0059289 | A1 * | 3/2012 | Nield | A61B 17/320068 601/2 |
| 2012/0116266 | A1 | 5/2012 | Houser et al. | |
| 2012/0116388 | A1 | 5/2012 | Houser et al. | |
| 2013/0289592 | A1 | 10/2013 | Stulen et al. | |
| 2014/0200544 | A1 | 7/2014 | Ryotokuji | |
| 2017/0224403 | A1 | 8/2017 | Suzuki et al. | |
| 2018/0370104 | A1 * | 12/2018 | Günther | B29C 45/2725 |

FOREIGN PATENT DOCUMENTS

| | | | | |
|---|---|---|---|---|
| JP | 2007-188945 | A | 7/2007 | |
| JP | 2013-545532 | A | 12/2013 | |
| JP | 2015-516231 | A | 6/2015 | |
| WO | WO-2010135502 | A1 * | 11/2010 | A61B 17/22004 |
| WO | 2012/061640 | A1 | 5/2012 | |
| WO | 2013/027688 | A1 | 2/2013 | |
| WO | 2013/165842 | A1 | 11/2013 | |
| WO | 2016/067739 | A1 | 5/2016 | |

OTHER PUBLICATIONS

Sep. 28, 2023 Office Action issued in Chinese Application No. 201880092938.7.

* cited by examiner

MEDICAL APPARATUS REMANUFACTURING METHOD

CROSS-REFERENCE TO RELATED APPLICATION

This application is a continuation of International Application No. PCT/JP2018/025876, filed on Jul. 9, 2018, the entire contents of which are incorporated herein by reference.

BACKGROUND

1. Technical Field

The present disclosure relates to a medical apparatus remanufacturing method.

2. Related Art

In the related art, there has been a proposed casing structure in which an electric device or the like is easily disassembled for recycling, and a disassembling method of the structure.

The casing structure includes an upper case having a fixing boss and a lower case having a receiving boss that are joined with each other by a fixing screw. Here, a plurality of thin recesses and ribs for separating the recesses are provided around the base of the fixing boss. When disassembling the upper case and the lower case from each other, a hammer is used to strike the fixing boss in a state where a cylindrical destruction jig is applied to the recess provided around the fixing boss of the upper case, thereby separating the fixing boss from the upper case. This facilitates disassembly of the upper case and the lower case from each other even in a case where the fixing screw has corrupted.

SUMMARY

The present disclosure is directed to a medical apparatus remanufacturing method. The method includes disassembling a housing including a first housing and a second housing. The first housing can include a boss that is press-fitted to a boss hole of a press-fitted portion of a second housing to form an assembled state in which the first housing and the second housing are assembled to each other. The disassembling includes changing a temperature of at least one of the boss and the press-fitted portion to decrease a contact surface pressure between the boss and the boss hole, and removing the boss from the boss hole to release the assembled state.

In some embodiments, the housing can be disassembled by heating at least one of the boss and the press-fitted portion so as to thermally deform a portion of one of the boss and the boss hole that contacts the other of the boss and the boss hole in the assembled state to decrease a contact surface pressure between the boss and the boss hole; and removing the boss from the boss hole to release the assembled state.

In some embodiments, the method can further include reassembling the first housing and the second housing to each other after disassembling the housing; and then performing a sterilization treatment that includes sending a sterilizing gas to the boss hole through a flow channel that allows passage of fluid and is provided between an outer surface of the boss and an inner surface of the boss hole.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments of a medical apparatus remanufacturing method will be described with reference to the accompanying drawings. Note that the embodiments of the medical apparatus remanufacturing method are not limited to the embodiments described below. In the drawings, same reference signs are attached to the same components.

Schematic Configuration of Treatment Tool

Figure 1:
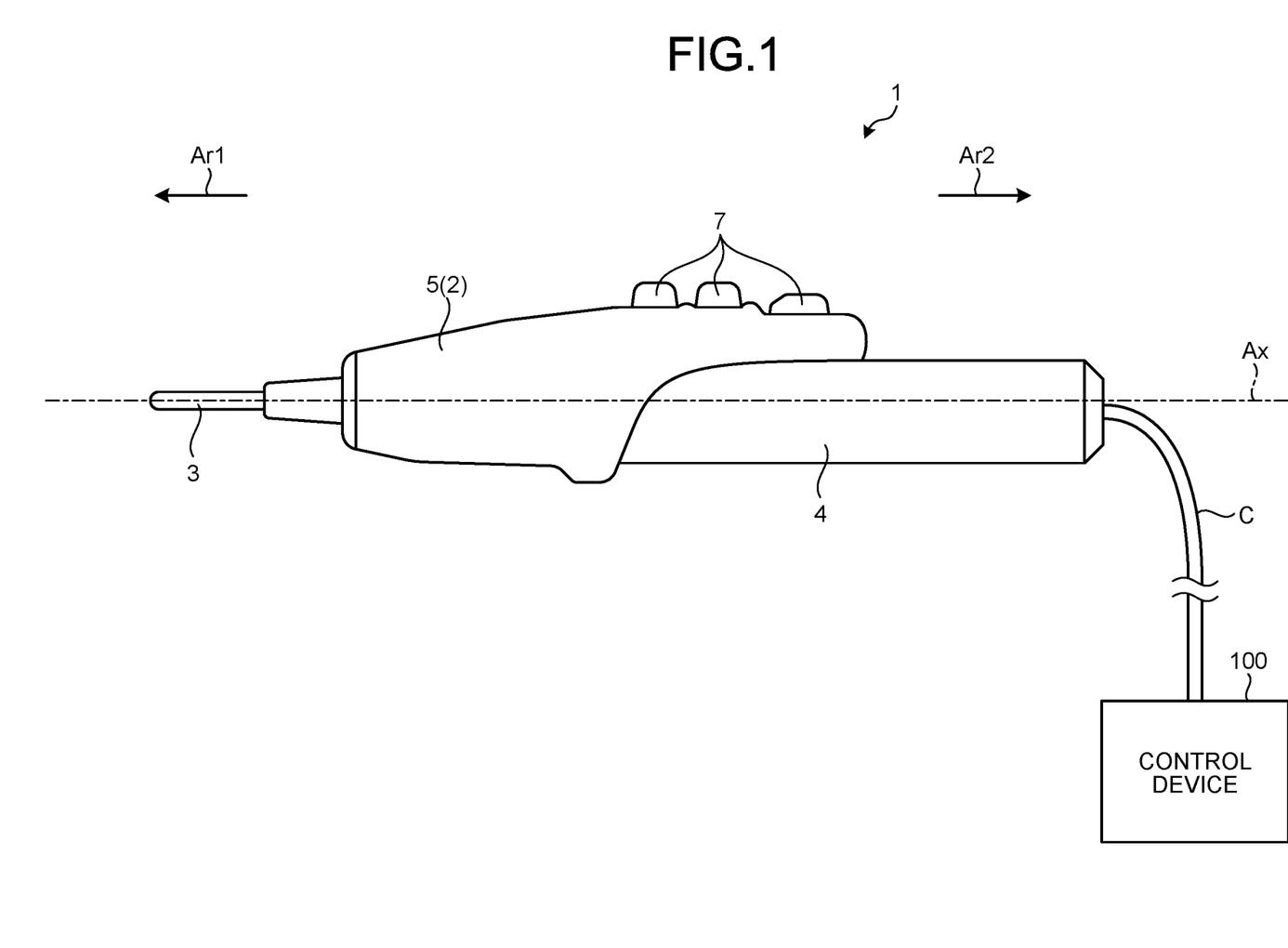
FIG. 1 is a view illustrating a treatment tool according to an exemplary embodiment.

FIG. 1 is a view illustrating a treatment tool 1 according to the present embodiment.

The treatment tool 1 corresponds to the medical apparatus. The treatment tool 1 applies ultrasound energy and radio-frequency energy to a site to be treated (hereinafter, referred to as a target site) in a biological tissue, thereby treating the target site. Here, the treatment typically means coagulation and incision of the target site. As illustrated in FIG. 1, the treatment tool 1 includes a housing 2, an ultrasound probe 3, and an ultrasound transducer 4.

Figure 2:
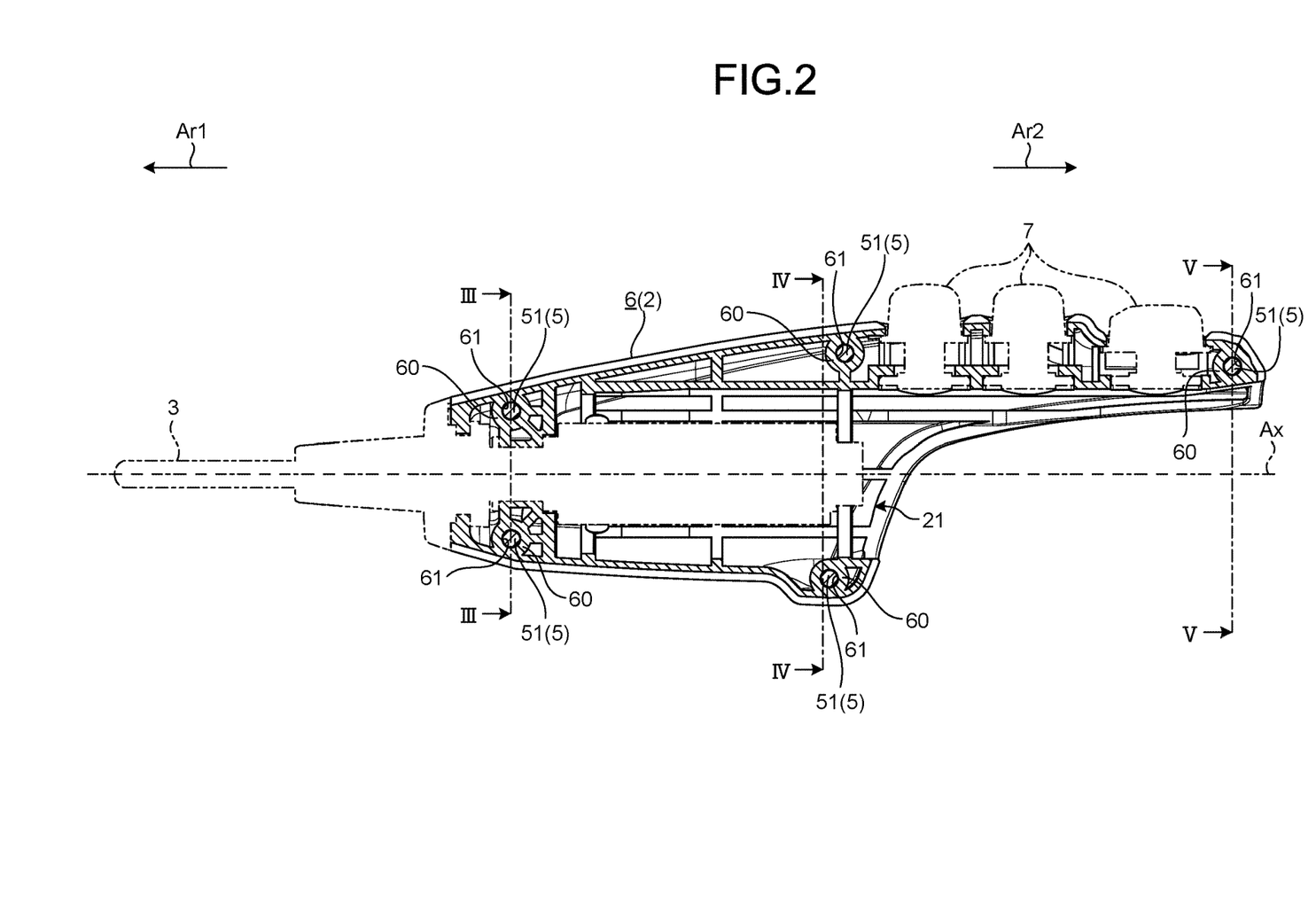
FIG. 2 is a view illustrating a housing.
Figure 3:
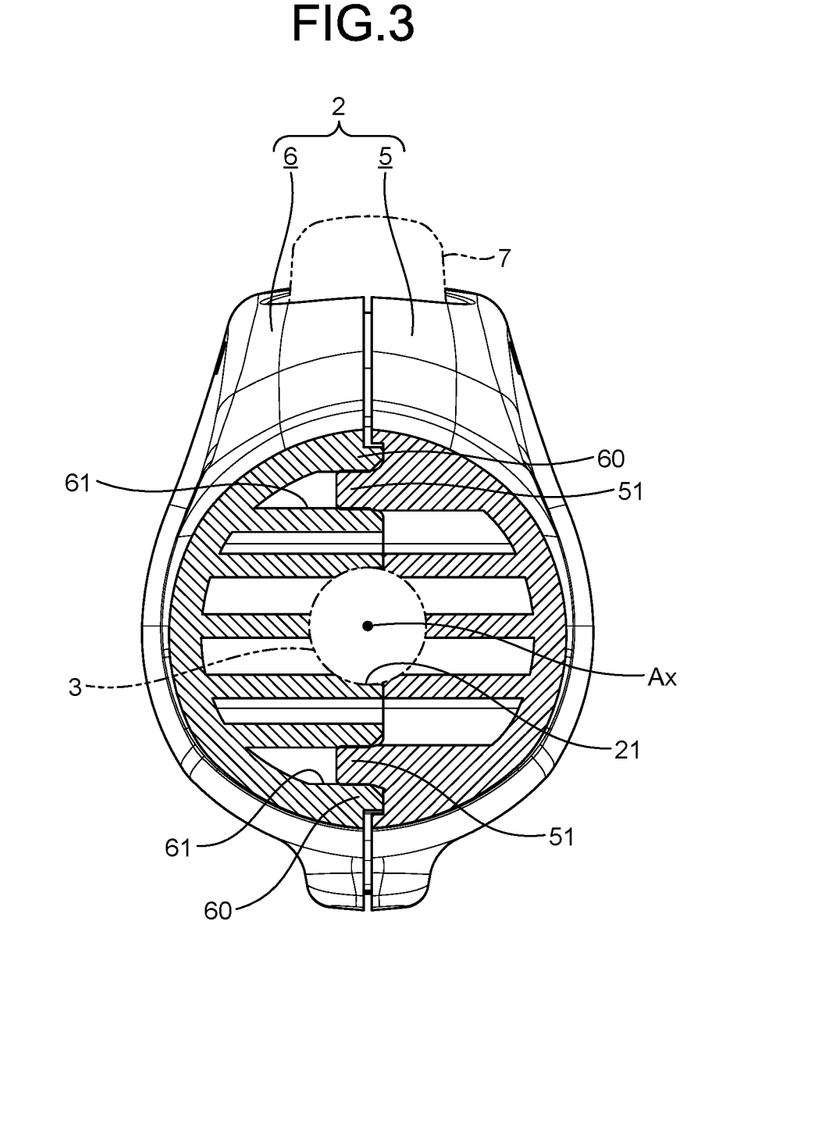
FIG. 3 is a cross-sectional view of the housing taken along line III-III illustrated in FIG. 2.
Figure 4:
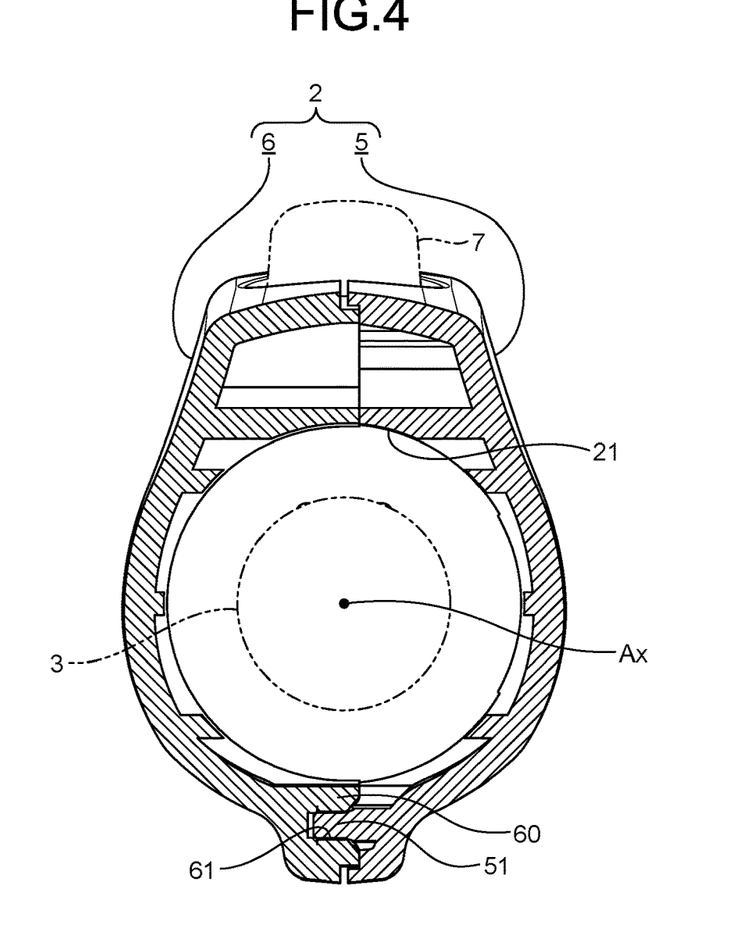
FIG. 4 is a cross-sectional view of the housing taken along line IV-IV illustrated in FIG. 2.
Figure 5:
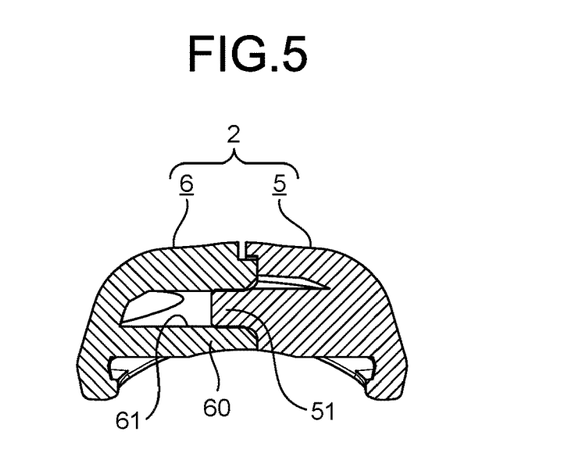
FIG. 5 is a cross-sectional view of the housing taken along line V-V illustrated in FIG. 2.

FIG. 2 is a view illustrating the housing 2. Specifically, FIG. 2 is a cross-sectional view of the housing 2 cut by a plane passing through a central axis Ax of the ultrasound probe 3. The plane corresponds to a boundary surface between first and second housings 5 and 6. FIG. 3 is a cross-sectional view of the housing 2 taken along line III-III illustrated in FIG. 2. FIG. 4 is a cross-sectional view of the housing 2 taken along line IV-IV illustrated in FIG. 2. FIG. 5 is a cross-sectional view of the housing 2 taken along line V-V illustrated in FIG. 2.

In the following, one side running along the central axis Ax of the ultrasound probe 3 will be referred to as a distal end side Ar1 (FIGS. 1 and 2), while the other side will be referred to as a proximal end side Ar2 (FIGS. 1 and 2).

The housing 2 is formed with two members, a first housing 5 and a second housing 6, as illustrated in FIGS. 2 to 5. The housing 2 is built by assembling the first and second housings 5 and 6 to each other. In an assembled state where the first and second housings 5 and 6 are assembled to each other, a channel 21 (FIGS. 2 to 4) penetrating along the central axis Ax (FIGS. 1 to 5) of the ultrasound probe 3 is provided. That is, the housing 2 has a tubular shape.

On an outer edge side of the inner surface of the first housing 5, a plurality (five in the present embodiment) of bosses 51 having columnar shapes are individually formed to protrude toward the second housing 6 side, as illustrated in FIGS. 2 to 5. In contrast, at individual positions facing the plurality of bosses 51 on the inner surface of the second housing 6, press-fitted portions 60 are formed to individually protrude toward the first housing 5 side, as illustrated in FIGS. 2 to 5. In addition, each of the press-fitted portions 60 has a boss hole 61 having a circular shape in plan view and extending from the distal end toward the proximal end so as to be used as a hole into which the boss 51 is press-fitted. That is, the press-fitted portion 60 is a recess having a fitting surface that fits with the boss 51.

That is, the assembled state in which the first and second housings 5 and 6 are assembled to each other is formed by press-fitting the bosses 51 into the boss holes 61, individually.

The relationship between a first thermal expansion coefficient of the first housing 5 (boss 51) and a second thermal expansion coefficient of the second housing 6 (press-fitted portion 60) described above is set to the relationship: First thermal expansion coefficient <Second thermal expansion coefficient. Furthermore, the relationship between a first thermal conductivity of the first housing 5 (boss 51) and a second thermal conductivity of the second housing 6 (press-fitted portion 60) is set to the relationship: First thermal conductivity <Second thermal conductivity.

Here, examples of the resin material having a high thermal expansion coefficient include polyethylene (heat resistant temperature: 70° C. to 90° C.), polypropylene (heat resistant temperature: 100° C. to 140° C.), Acrylonitrile Butadiene Styrene (ABS) resin (heat resistant temperature: 70° C. to 100° C.). In contrast, examples of the resin material having a low thermal expansion coefficient include polycarbonate (heat resistant temperature: 120° C. to 130° C.), polytetrafluoroethylene (heat resistant temperature: 260° C.), and polysulfone (heat resistant temperature: 150° C.) Moreover, examples of the resin material having high thermal conductivity include polysulfone, and polyethylene. In contrast, examples of the resin material having low thermal conductivity include polycarbonate, PTFE, ABS, and polypropylene.

Therefore, for example, using polycarbonate for forming the first housing 5 and using polyethylene for forming the second housing 6 will make it possible to satisfy the two relations regarding the thermal expansion coefficient and the thermal conductivity described above.

Furthermore, as illustrated in FIG. 1 or 2, the housing 2 includes a plurality of (three in the present embodiment) switches 7.

The plurality of switches 7 is individually provided so as to be exposed to the outside of the housing 2 to receive an output start operation by the practitioner. Here, as illustrated in FIG. 1, the treatment tool 1 is electrically connected to a control device 100 via an electric cable C. In addition, the switch 7 outputs an operation signal corresponding to the output start operation to the control device 100 via the electric cable C.

The ultrasound probe 3, formed of a conductive material, has an elongate shape extending along the central axis Ax. The ultrasound probe 3 is mounted in the channel 21 of the housing 2 in a state where an end of the distal end side Ar1 is exposed to the outside. Note that the ultrasound probe 3 cannot be removed from the housing 2 unless the housing 2 is divided into the first and second housings 5 and 6. Furthermore, the ultrasound probe 3 is connected, at an end on the proximal end side Ar2, to a bolt-tightened Langevin transducer (BLT) included in the ultrasound transducer 4. Subsequently, the ultrasound probe 3 transmits the ultrasound vibration generated by the BLT from the end on the proximal end side Ar2 to the end on the distal end side Ar1. In the present embodiment, the ultrasound vibration is a longitudinal vibration that vibrates in the direction along the central axis Ax. At this time, the end of the ultrasound probe 3 on the distal end side Ar1 vibrates with a desired amplitude by the longitudinal vibration.

The ultrasound transducer 4 is to be inserted into the channel 21 from the proximal end side Ar2 of the housing 2 and configured to be detachable from the housing 2. Although not specifically illustrated, the ultrasound transducer 4 includes a BLT that generates ultrasound vibration in accordance with the supply of AC power.

The treatment tool 1 described above operates as follows.

A practitioner holds the treatment tool 1 by hand and brings the end of the ultrasound probe 3 on the distal end side Ar1 into contact with a target site. Thereafter, the practitioner presses the switch 7. Subsequently, the control device 100 executes the following control according to the operation signal from the switch 7.

The control device 100 supplies a radio-frequency current between the ultrasound probe 3 and an indifferent electrode (not illustrated) attached to the surface of the subject. Accordingly, a radio-frequency current flows through the target site. In other words, radio-frequency energy is applied to the target site.

Furthermore, the control device 100 supplies the AC power to the BLT included in the ultrasound transducer 4 at substantially the same time as the supply of the radio-frequency current between the ultrasound probe 3 and the indifferent electrode, thereby providing the BLT with ultrasound vibration. Subsequently, ultrasound vibration is applied to the target site from the end of the ultrasound probe 3 on the distal end side Ar1. In other words, ultrasound energy is applied to the target site.

Accordingly, a radio-frequency current flows through the target site, leading to generation of Joule heat. Furthermore, the longitudinal vibration of the ultrasound probe 3 generates frictional heat between the end of the ultrasound probe 3 on the distal end side Ar1 and the target site. This makes it possible to achieve incision with coagulation in the target site.

As described above, the treatment tool 1 according to the present embodiment has the functions of both the ultrasound treatment tool and the monopolar treatment tool.

Method of Remanufacturing Treatment Tool

Next, a method of remanufacturing the above-described treatment tool 1 will be described. The method of remanufacturing the treatment tool 1 corresponds to the medical apparatus remanufacturing method.

Figure 6:
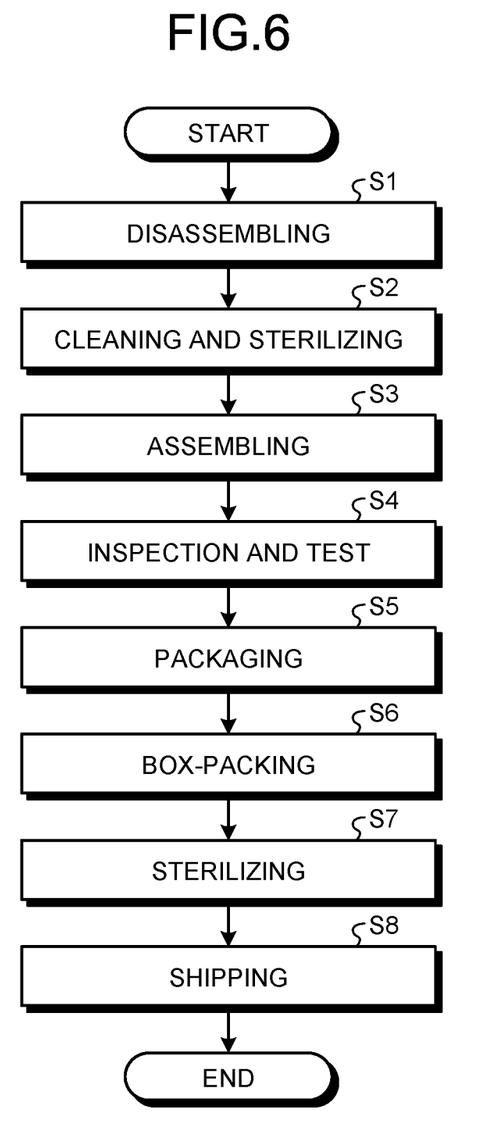
FIG. 6 is a flowchart illustrating a method of remanufacturing a treatment tool.

FIG. 6 is a flowchart illustrating a method of remanufacturing the treatment tool 1.

An operator collects the used treatment tool 1 after treating the target site. Subsequently, the operator disassembles the collected treatment tool 1 as described below (step S1).

Figure 7:
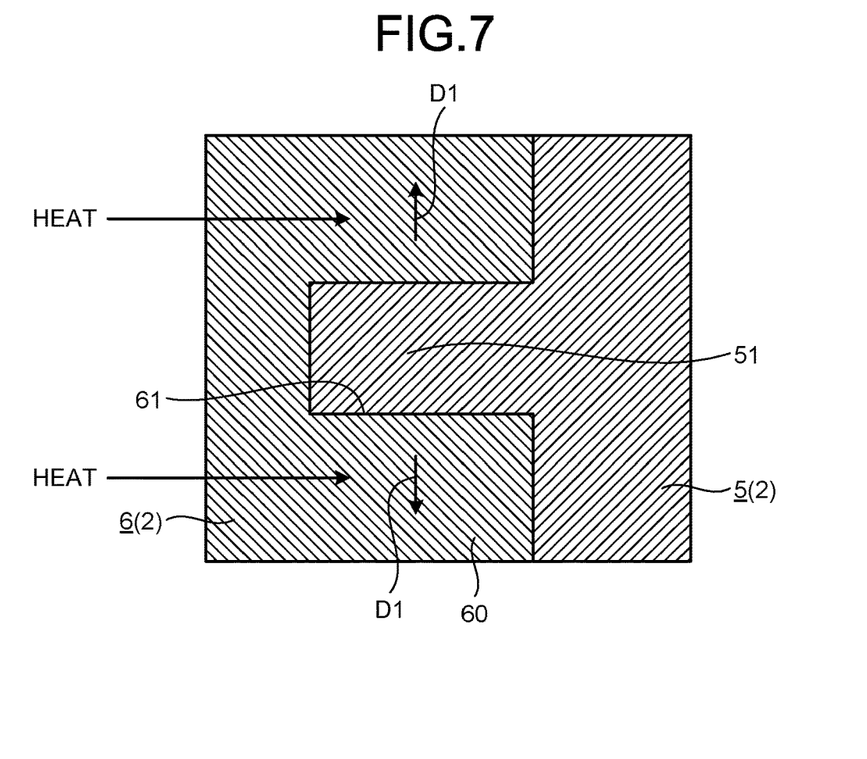
FIG. 7 is a view illustrating step S1 according to an exemplary embodiment.

FIG. 7 is a view illustrating step S1. For convenience of description, FIG. 7 simply illustrates portions joined to each other by the boss 51 and the boss hole 61, as the first and second housings 5 and 6.

First, the operator releases the assembled state of the first and second housings 5 and 6, and divides the housing 2 into two members, the first and second housings 5 and 6.

Specifically, the operator places the treatment tool 1 on a heating plate in a posture in which the second housing 6 comes at a lower portion and the first housing 5 at an upper portion. This allows the second housing 6 (press-fitted portion 60) to be heated from the outer surface side by the heat from the heating plate, as illustrated in FIG. 7 (temperature changing step). In the present embodiment, the temperature used for heating the second housing 6 is lower than the heat resistant temperature of the second housing 6. Accordingly, the boss hole 61 radially expands in direction D1 (FIG. 7) by thermal expansion. That is, the contact surface pressure between the boss 51 and the boss hole 61 decreases.

Thereafter, the operator removes the boss 51 from the boss hole 61 to divide the housing 2 into two members, the first and second housings 5 and 6 (releasing step). The operator then removes the ultrasound probe 3 from the housing 2.

After step S1, the operator cleans and sterilizes the ultrasound probe 3 removed from the housing 2 (step S2).

Specifically, cleaning of the ultrasound probe 3 is performed using a brush or the like to remove large stains attached to the ultrasound probe 3. Thereafter, in order to remove pathogenic microorganisms derived from blood, body fluid, mucosa, or the like, ultrasound cleaning of the ultrasound probe 3 is performed using one of cleaning solutions including a cleaning solution containing isopropanol, a proteolytic enzyme detergent, or alcohol. Note that the cleaning solution is not limited to the above-described cleaning solution, and other cleaning solution may be adopted or a disinfecting liquid may be contained.

Furthermore, in the sterilization of the ultrasound probe 3, one of high-pressure steam sterilization, ethylene oxide gas sterilization, or hydrogen peroxide gas low-temperature sterilization is used in order to remove pathogenic microorganisms or the like derived from blood, body fluid, mucosa, or the like.

After step S2, the operator assembles a new treatment tool 1 (step S3: assembling step).

Specifically, the operator reuses the first and second housings 5 and 6 divided into two members in step S1. Subsequently, the operator inserts the ultrasound probe 3 cleaned and sterilized in step S2 between the first and second housings 5 and 6, and presses the boss 51 into the boss hole 61 to newly assemble the new treatment tool 1.

After step S3, the operator inspects and tests (step S4) the treatment tool 1 newly assembled in step S2.

Specifically, examples of the inspection and test of the treatment tool 1 include various verification tests such as biocompatibility, cleaning validation, performance, ethylene oxide gas (EOG) sterilization residue test, bioburden resistance test, comparative resistance of sterilization, and viable cell count test. Here, regarding the performance, verification is performed to verify that the newly formed treatment tool 1 has the same effectiveness and safety as the original product.

After step S4, the operator sequentially performs packaging (step S5), box-packing (step S6), sterilization (step S7: sterilization step) and shipment (step S8) of the treatment tool 1 verified to have the same effectiveness and safety as the original product by the inspection and test in step S4.

Here, in step S7, a sterilization treatment using a sterilizing gas such as ethylene oxide gas or propylene oxide gas is applied to the treatment tool 1 box-packed in step S6.

Steps S1 to S8 described above are executed to achieve remanufacturing of the treatment tool 1.

The present embodiment described above achieves the following effects.

In the method of remanufacturing the treatment tool 1 according to the present embodiment, the second housing 6 (press-fitted portion 60) is heated in step S1. Subsequently, the boss hole 61 radially expands due to thermal expansion. That is, the contact surface pressure between the boss 51 and the boss hole 61 decreases. Therefore, the operator can disassemble the housing 2 without causing a damage in the housing 2 and can reuse the housing 2 when remanufacturing the treatment tool 1.

Meanwhile, if the first thermal expansion coefficient of the first housing 5 (boss 51) was high (for example, higher than the second thermal expansion coefficient of the second housing 6), the boss 51 would thermally expand due to the heat transferred from the second housing 6 in the radially expanding direction in step S1, similar to the boss hole 61. This would make it difficult to reduce the contact surface pressure between the boss 51 and the boss hole 61.

Fortunately however, the method of remanufacturing the treatment tool 1 according to the present embodiment heats, in step S1, the second housing 6 (the press-fitted portion 60) having a thermal expansion coefficient higher than that of the first housing 5 (boss 51). Therefore, even when the boss 51 thermally expands due to the heat transferred from the second housing 6, the thermal expansion amount can be suppressed. That is, it is possible to easily decrease the contact surface pressure between the boss 51 and the boss hole 61.

In particular, the second thermal conductivity of the second housing 6 (press-fitted portion 60) is higher than the first thermal conductivity of the first housing 5 (boss 51). Therefore, the second housing 6 can be quickly heated to the target temperature. Furthermore, heat transfer from the second housing 6 (press-fitted portion 60) to the boss 51 can be suppressed. That is, it is possible to suppress thermal expansion in the radially expanding direction of the boss 51.

Figure 8:
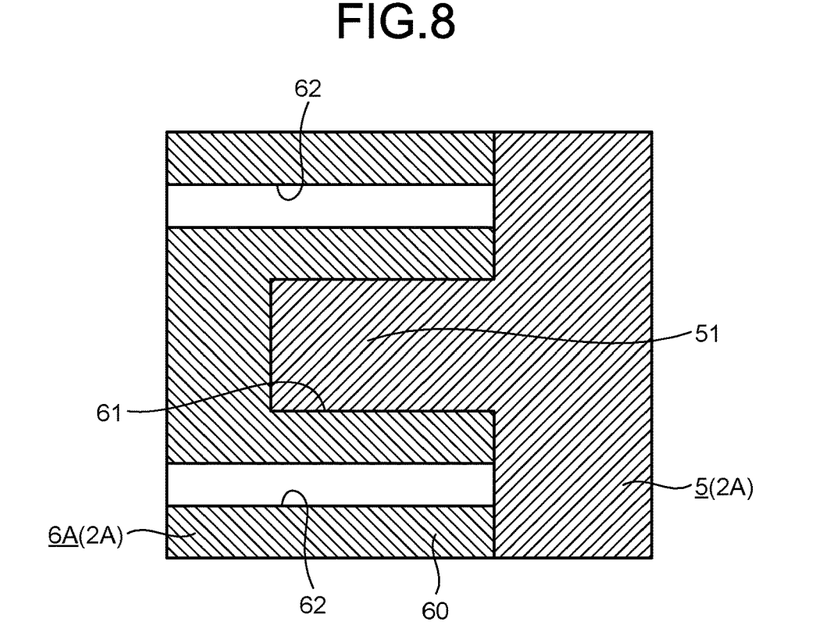
FIG. 8 is a view illustrating step S1 according to an exemplary embodiment.

FIG. 8 is a view corresponding to FIG. 7, illustrating another exemplary embodiment.

A housing 2A (second housing 6A) according to the exemplary embodiment shown in in FIG. 8 is only different from the second housing 6 of the above-described embodiment shown in FIG. 7 in that a hole 62 is formed, as illustrated in FIG. 8.

As illustrated in FIG. 8, the hole 62 penetrates from the outer surface of the second housing 6A to the distal end of the press-fitted portion 60. In the present embodiment, the hole 62 is provided in plurality at positions close to the boss hole 61, at positions surrounding the boss hole 61.

Subsequently, in the present embodiment, in step S1, the operator sends a hot fluid such as hot air from the outer surface of the second housing 6A to flow into the hole 62, thereby heating the second housing 6A (press-fitted portion 60). In the present embodiment, the temperature for heating the second housing 6A is lower than the heat resistant temperature of the second housing 6A, similarly to the above-described embodiment.

The present embodiment described above achieves the following effect in addition to effects similar to those of the embodiment described above.

In the present embodiment, in step S1, the second housing 6A (press-fitted portion 60) is heated through the hole 62 extending from the outer surface of the second housing 6A toward the press-fitted portion 60. This makes it possible to intensively heat the press-fitted portion 60 in the second housing 6A. That is, it is possible, in executing the step S1, to avoid an adverse effect caused by heating sites of the treatment tool 1 other than the press-fitted portion 60.

In the present embodiment, an additional hole may be further provided in the second housing 6A to allow the hot fluid flowing into the hole 62 to flow out of the housing 2A.

Figure 9:
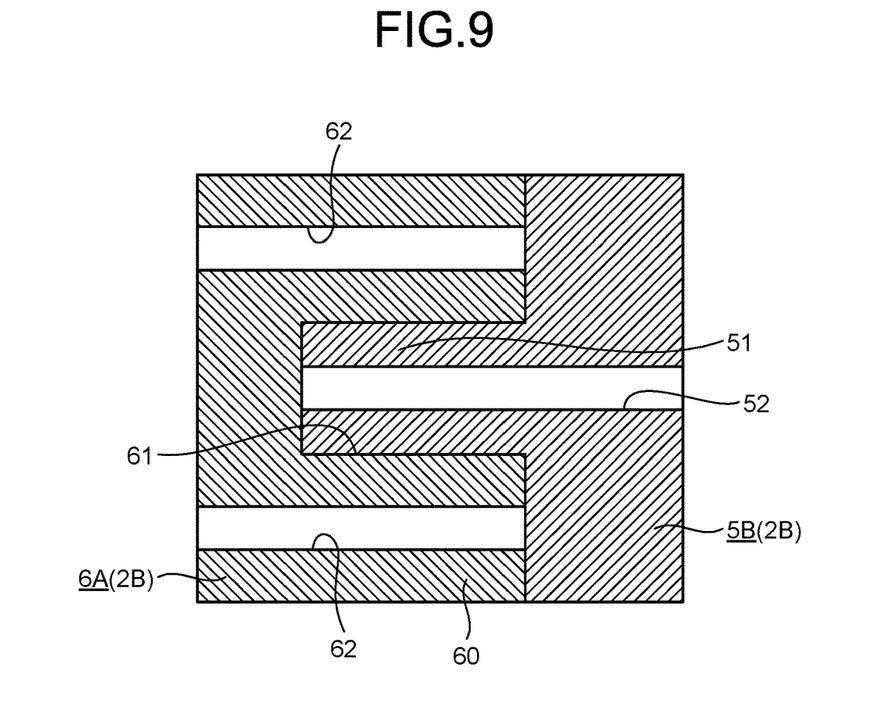
FIG. 9 is a view illustrating step S1 according to an exemplary embodiment.

FIG. 9 is a view corresponding to FIG. 7, illustrating another exemplary embodiment.

While the second housing 6 (press-fitted portion 60) is heated in step S1 in the above-described embodiment, it is also allowable to further perform cooling of the first housing 5 (boss 51).

At this time, it is also allowable to form a hole 52 on the first housing 5 described in the above-described embodiment, like a housing 2B (first housing 5B) according to the present embodiment illustrated in FIG. 9.

As illustrated in FIG. 9, the hole 52 penetrates from the outer surface of the first housing 5B to the distal end of the boss 51.

Subsequently, in the present embodiment, the operator sends, in step S1, a hot fluid such as hot air from the outer surface of the second housing 6A to flow into the hole 62, thereby heating the second housing 6A (press-fitted portion 60), similarly to the above-described embodiment shown in FIG. 8. At the same time, the operator cools the first housing 5B (boss 51) by injecting a cooling fluid such as cooling air into the hole 52 from the outer surface of the first housing 5B. Subsequently, the boss hole 61 radially expands due to thermal expansion. In contrast, the boss 51 radially shrinks due to contraction accompanying cooling.

The present embodiment described above achieves the following effect in addition to effects similar to those of the embodiments illustrated in FIGS. 7 and 8 and described above.

In the present embodiment, the second housing 6A (press-fitted portion 60) is heated and the first housing 5B (boss 51) is cooled in step S1. Subsequently, the boss hole 61 radially expands due to thermal expansion. Furthermore, the boss 51 radially shrinks due to contraction accompanying cooling. This makes it possible to effectively decrease the contact surface pressure between the boss 51 and the boss hole 61.

Furthermore, in the present embodiment, step S1 cools the first housing 5B (boss 51) through the hole 52 extending inward from the outer surface of the first housing 5B. This makes it possible to intensively cool the site in the first housing 5B where the boss 51 is provided. That is, it is possible, in executing the step S1, to avoid an adverse effect caused by cooling sites of the treatment tool 1 other than the portion where the boss 51 is provided.

In the present embodiment, an additional hole may be further provided in the second housing 6A to allow the hot fluid flowing into the hole 62 to flow out of the housing 2B. Similarly, the first housing 5B may be further provided with a hole for allowing the cooling fluid flowing into the hole 52 to flow out of the housing 2B.

Furthermore, while step S1 in the present embodiment heats the second housing 6A (press-fitted portion 60) while cooling the first housing 5B (boss 51), the disclosure is not limited to this. It is also allowable to execute only cooling of the first housing 5B (boss 51) without heating the second housing 6A (press-fitted portion 60).

Figure 10:
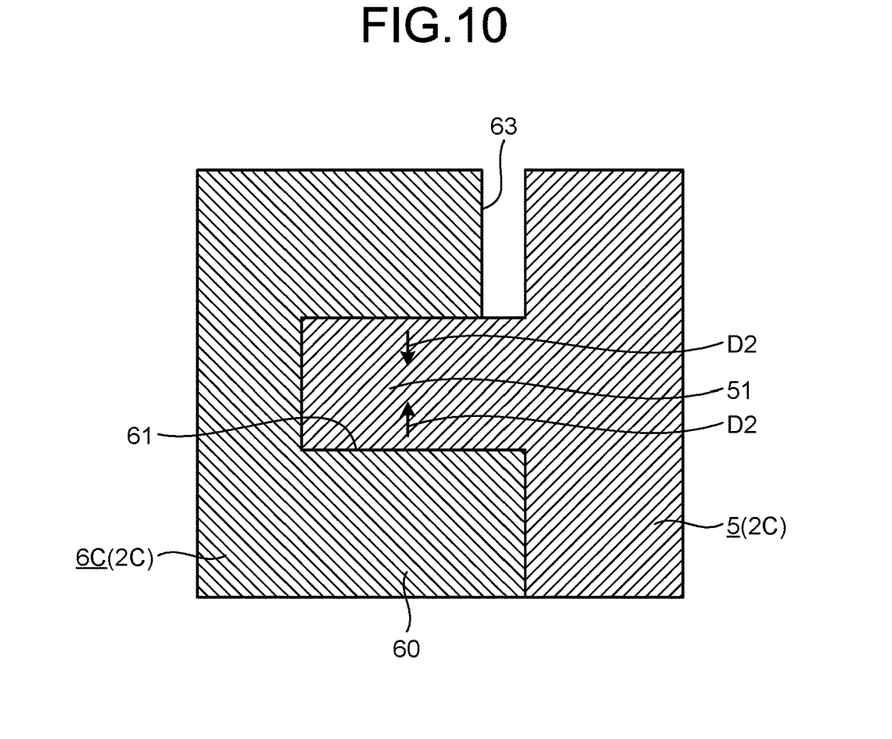
FIG. 10 is a view illustrating step S1 according to an exemplary embodiment.
Figure 11:
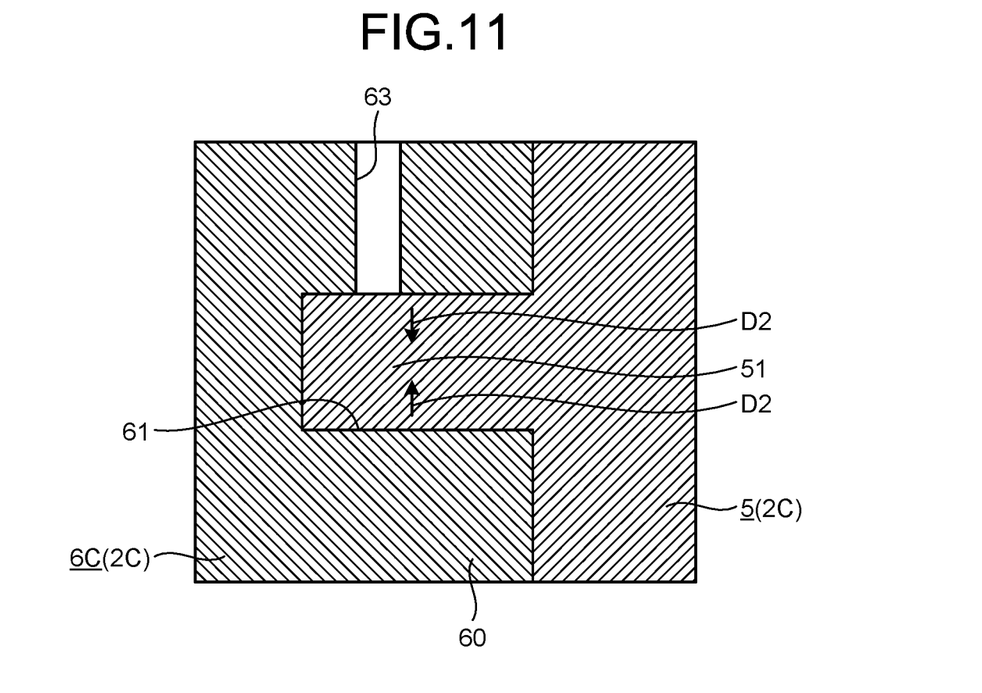
FIG. 11 is a view illustrating step S1 according to an exemplary embodiment.

FIGS. 10 and 11 are views corresponding to FIG. 7, illustrating another exemplary embodiment.

In the embodiment described above, in step S1, the contact surface pressure between the boss 51 and the boss hole 61 is decreased by the thermal expansion of the boss hole 61. However, the disclosure is not limited to this, and creep deformation of the boss 51 may be used to decrease the contact surface pressure.

Specifically, the operator heats the first housing 5 (boss 51) to the heat resistant temperature or higher in step S1. This increases the strain rate of creep deformation in the boss 51 in the radially shrinking direction D2 (FIGS. 10 and 11). This decreases the contact surface pressure between the boss 51 and the boss hole 61.

At this time, it is also allowable to form a hole 63 on the second housing 6 described in the above-described embodiment, like the housing 2C (second housing 6C) according to the present embodiment illustrated in FIG. 10 or 11.

As illustrated in FIG. 10 or 11, the hole 63 penetrates from the outer surface of the second housing 6C to the inner circumferential surface of the boss hole 61. More specifically, the hole 63 extends in a direction orthogonal to the longitudinal direction from the proximal end to the distal end on the boss 51 while exposing a part of an outer circumferential surface of the boss 51 to the outside of the housing 2C. The hole 63 may be formed at the proximal end side of the boss 51 as illustrated in FIG. 10 or at the distal end side of the boss 51 as illustrated in FIG. 11.

Subsequently, in the present embodiment, in step S1, the operator sends a hot fluid such as hot air from the outer surface of the second housing 6C to flow into the hole 63, thereby heating the boss 51.

Even in a case where the contact surface pressure between the boss 51 and the boss hole 61 is decreased by using the creep deformation of the boss 51 as in the present embodiment described above, it is possible to achieve an effect similar to that of the above-described embodiment.

Furthermore, in the present embodiment, in step S1, the first housing 5 (boss 51) is heated through the hole 63 extending inward from the outer surface of the second housing 6C. This makes it possible to intensively heat the boss 51. That is, it is possible, in executing the step S1, to avoid an adverse effect caused by heating sites of the treatment tool 1 other than the boss 51.

In the present embodiment, an additional hole may be further provided in the first housing 5 or the second housing 6C to allow the hot fluid flowing into the hole 63 to flow out of the housing 2C.

It is also allowable in the present embodiment to decrease the contact surface pressure between the boss 51 and the boss hole 61 by using the creep deformation of the boss hole 61. That is, in step S1, the second housing 6C (press-fitted portion 60) is heated to the heat resistant temperature or higher. This increases the strain rate of creep deformation in the boss hole 61 in the radially expanding direction. This decreases the contact surface pressure between the boss 51 and the boss hole 61.

Figure 12A:
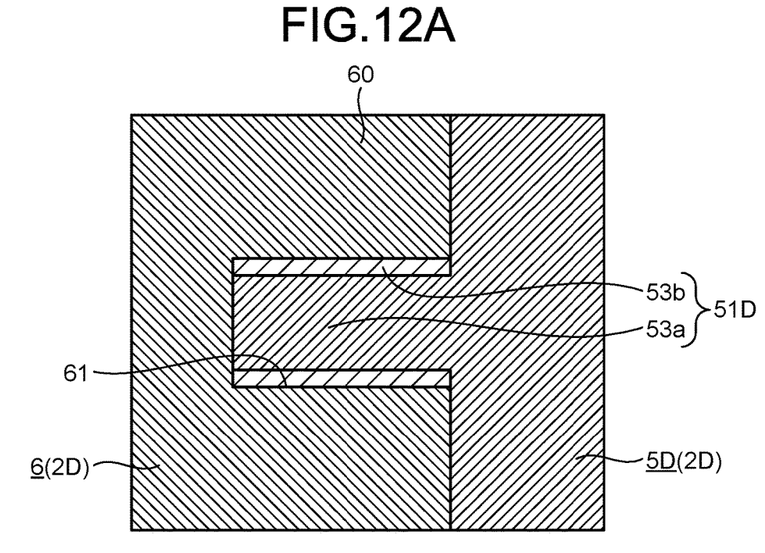
FIGS. 12A and 12B are views illustrating step S1 according to an exemplary embodiment.
Figure 12B:
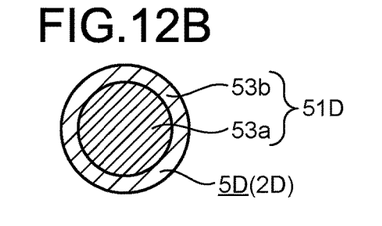

FIGS. 12A and 12B are views illustrating another exemplary embodiment. Specifically, FIG. 12A corresponds to FIG. 7. FIG. 12B is a cross-sectional view of a boss 51D cut by a plane orthogonal to the longitudinal direction from the proximal end to the distal end of the boss 51D.

A housing 2D (first housing 5D) according to the present embodiment is only different from the above-described embodiment in that the boss 51 has a modified configuration, as illustrated in FIGS. 12A and 12B.

Specifically, the boss 51D according to the present embodiment includes a boss body 53a and an adjusting member (portion or surface portion) 53b, as illustrated in FIGS. 12A and 12B.

The boss body 53a has the same shape as the boss 51 described in the above-described embodiment.

As illustrated in FIGS. 12A and 12B, the adjusting member 53b is provided over the entire outer circumferential surface of the boss body 51a so as to form an outer circumferential surface of the boss 51D. That is, the adjusting member 53b comes in contact with the inner circumferential surface of the boss hole 61 in a state where the boss 51D is press-fitted into the boss hole 61. Examples of materials for the adjusting member 53b include resin materials such as polyamide (heat resistant temperature: 80° C. to 140° C.), polymethylmethacrylate (heat resistant temperature: 70° C. to 90° C.), polyethylene, polyvinyl alcohol (heat resistant temperature: 40° C. to 80° C.)

In the present embodiment, in step S1, the operator heats the first housing 5D (boss 51D) to the heat resistant temperature of the adjusting member 53b or higher. This increases the strain rate in creep deformation (thermal deformation) in the radially shrinking direction in the adjusting member 53b. This decreases the contact surface pressure between the boss 51D and the boss hole 61.

The present embodiment described above achieves the following effect in addition to effects similar to those of the embodiment described above.

In the present embodiment, the contact surface pressure between the boss 51D and the boss hole 61 is decreased by using the creep deformation of the adjusting member 53b. That is, since there is no need to use the creep deformation of the boss body 53a, it is possible to improve the degree of freedom in selecting the material forming portions other than the adjusting member 53b in the first housing 5D.

In the present embodiment, the adjusting member (portion) 53b need not necessarily be formed on the outer circumferential surface of the boss 51D, and may be formed on the inner circumferential surface of the boss hole 61.

In addition, the configuration of the exemplary embodiments described above, such as that illustrated in FIGS. 10 and 11, may be combined with the present embodiment.

Figures 13A, 13B, 13C:
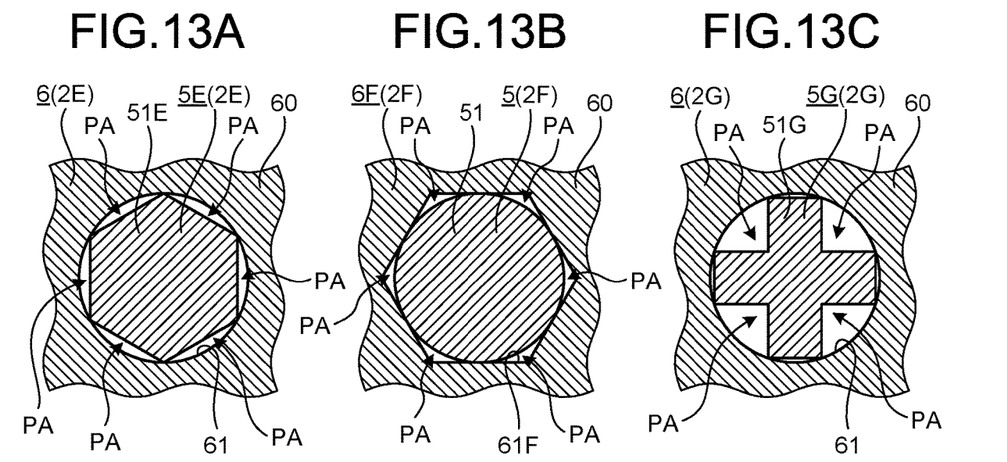
FIGS. 13A to 13C are views illustrating step S1 according to an exemplary embodiment.

FIGS. 13A to 13C are views illustrating another exemplary embodiment. Specifically, FIGS. 13A to 13C are cross-sectional views of portions of housings 2E to 2G according to the present embodiment that are joined to each other by bosses 51, 51E, and 51G and the boss holes 61 and 61F, which are respectively cut by a plane orthogonal to the longitudinal direction of the bosses 51, 51E, and 51G.

While the above-described embodiment has the boss 51 formed in a columnar shape and the boss hole 61 formed in a circular shape in plan view, the disclosure is not limited to this.

For example, as illustrated as the housing 2E (first housing 5E) according to the present embodiment illustrated in FIG. 13A, it is allowable to adopt the boss 51E having a hexagonal cross section.

In addition, for example, as illustrated as the housing 2F (second housing 6F) according to the present embodiment illustrated in FIG. 13B, it is allowable to adopt the boss hole 61F having a hexagonal shape in plan view.

Furthermore, for example, as illustrated as the housing 2G (first housing 5G) according to the present embodiment illustrated in FIG. 13C, it is allowable to adopt the boss 51G having a cross-shaped cross section.

The present embodiment described above achieves the following effect in addition to effects similar to those of the embodiment described above.

In the present embodiment, a flow channel PA that allows passage of the fluid is provided between the outer circumferential surface of the boss 51, 51E, or 51G and the inner circumferential surface of the boss hole 61 or 61F, extending in the longitudinal direction running from the proximal end to the distal end of the boss 51, 51E, or 51G. Therefore, in step S7, the sterilizing gas flows into the boss hole 61 or 61F through the flow channel PA. That is, the sterilization treatment using the sterilizing gas can be appropriately executed.

Furthermore, in the present embodiment, it is possible to reduce the contact area between the outer circumferential surface of the bosses 51, 51E, or 51G and the inner circumferential surface of the boss holes 61 or 61F. This makes it possible, in step S1, to suppress the heat transfer from the second housing 6 or 6F (press-fitted portion 60) to the boss 51, 51E, or 51G. That is, it is possible to suppress thermal expansion in the radially expanding direction of the boss 51, 51E, or 51G.

In addition, the configurations of the exemplary embodiments described above, such as those illustrated in FIGS. 7 to 12B, may be combined with the present embodiment. Here, when the configuration of the embodiment shown in FIGS. 12A and 12B described above is combined with the present embodiment (FIGS. 13A-13B), the adjusting member (portion) 53b is preferably provided at a site where the outer circumferential surfaces of the bosses 51, 51E, or 51G comes in contact with the boss hole 61 or 61F.

Figure 14A:
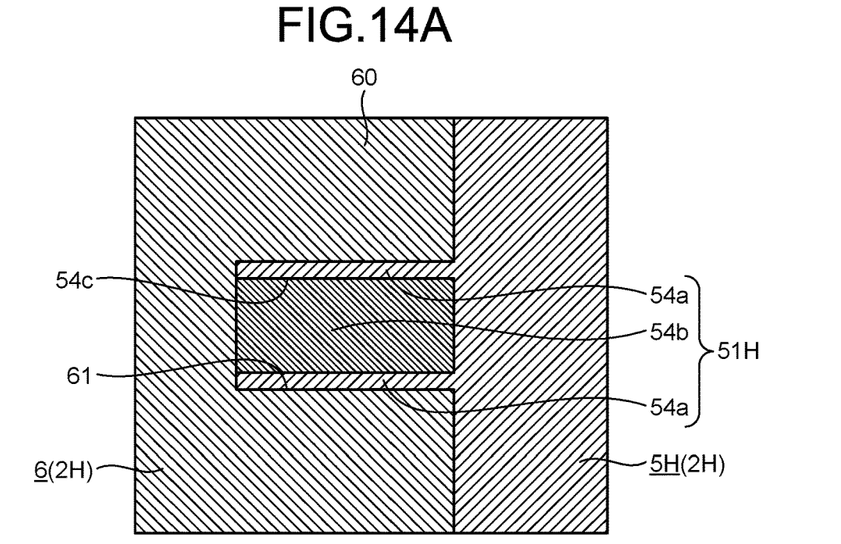
FIGS. 14A and 14B views illustrating step S1 according to an exemplary embodiment.
Figure 14B:
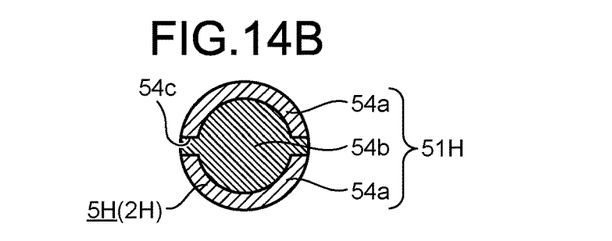

FIGS. 14A and 14B views illustrating another exemplary embodiment. Specifically, FIG. 14A corresponds to FIG. 7. FIG. 14B is a cross-sectional view of a boss 51H cut by a plane orthogonal to the longitudinal direction running from the proximal end to the distal end of the boss 51H.

A housing 2H (first housing 5H) according to the present embodiment is only different from the above-described embodiment in that the boss 51 has a modified configuration, as illustrated in FIGS. 14A and 14B.

Specifically, the boss 51H according to the present embodiment includes a boss body 54a and an adjusting member (portion) 54b, as illustrated in FIGS. 14A and 14B.

A boss body 54a has the same outer shape as the boss 51 described in the above-described embodiment. Subsequently, as illustrated in FIGS. 14A and 14B, the boss body 54a has a cutout 54c that extends from the distal end toward the proximal end side of the boss body 54a to divide the boss body 54a into two members in the radial direction.

The adjusting member 54b is embedded in the cutout 54c, as illustrated in FIGS. 14A and 14B. The adjusting member 54b can be formed by employing the material same as the material of the adjusting member 53b described above with respect to the embodiment shown in FIGS. 12A and 12B.

In the present embodiment, in step S1, the operator heats the first housing 5H (boss 51H) to the heat resistant temperature of the adjusting member 54b or higher. This increases the strain rate in creep deformation (thermal deformation) in the radially shrinking direction in the adjusting member 54b. That is, the boss body 54a divided into two members by the cutout 54c is inclined in a direction in which the boss body 54a approaches in the radial direction. This decreases the contact surface pressure between the boss 51H and the boss hole 61.

The present embodiment described above achieves the effects similar to those of the embodiments described above, including the embodiments shown in FIGS. 7, 12A, and 12B.

In addition, the configuration of the embodiments described above, such as the embodiment illustrated in FIGS. 10 and 11, may be combined with the present embodiment.

Figure 15:
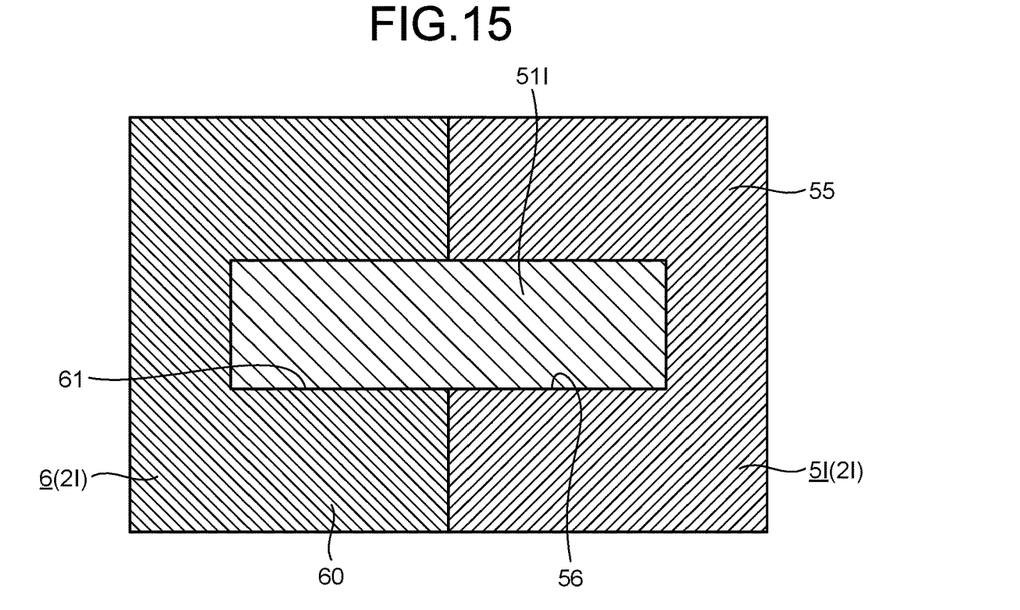
FIG. 15 is a view illustrating step S1 according to an exemplary embodiment.

FIG. 15 is a view corresponding to FIG. 7, illustrating another exemplary embodiment.

Although the boss 51 is integrally formed with the first housing 5 in the above-described embodiment, the disclosure is not limited to this.

As illustrated in FIG. 15, a housing 2I (first housing 5I) according to the present embodiment includes a first housing body 55 and a boss 51I.

The first housing body 55 is different from the first housing 5 described in the above-described embodiment in that the boss 51 is omitted and a press-fitting hole 56 into which the boss 51I is press-fitted is formed at the formation position of the boss 51.

The boss 51I is formed of a metal material. That is, the thermal expansion coefficient of the boss 51I is lower than that of the first housing body 55 and the second housing 6 (press-fitted portion 60). Furthermore, the boss 51I is press-fitted into the press-fitting hole 56. In addition, the boss 51I is press-fitted into the boss hole 61 when the first and second housings 5I and 6 are assembled to each other.

Even in a case where the boss 51I is provided separately from the first housing body 55 as in the present embodiment described above, it is possible to achieve an effect similar to that of the above-described embodiment.

In addition, the configurations of any of the embodiments described above, such as those shown in FIGS. 7 to 14B, may be combined with the present embodiment.

Hereinabove, the aspects of the disclosure has been described, but the disclosure is not limited to the exemplary embodiments described above.

The above-described embodiments adopt the treatment tool 1 as the medical apparatus according to the disclosure. The disclosure is not limited to this, and another medical apparatus may be adopted as the medical apparatus according to the disclosure.

While the above-described embodiments have a configuration in which the treatment tool 1 applies both ultrasound energy and radio-frequency energy to the target site, the disclosure is not limited to this. For example, the treatment tool 1 may be configured to apply ultrasound energy alone to the target site. Furthermore, the treatment tool 1 may be configured to apply radio-frequency energy alone to the target site. Furthermore, the treatment tool 1 may be configured to transfer heat from a heater to the target site to treat the target site.

According to the medical apparatus remanufacturing method, it is possible to disassemble the housing without causing a damage in the housing and possible to reuse the housing.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical apparatus remanufacturing method comprising:
    disassembling a housing including a first housing and a second housing, the first housing including a boss that is press-fitted to a boss hole of a press-fitted portion of the second housing in an assembled state in which the first housing and the second housing are assembled to each other, the disassembling including:
        heating the press-fitted portion through a hole formed in the second housing so as to thermally expand the boss hole to decrease a contact surface pressure between the boss and the boss hole, the hole extending from an opening at an outer surface of the second housing toward the press-fitted portion; and
        removing the boss from the boss hole to release the assembled state.

2. The medical apparatus remanufacturing method according to claim 1, further comprising
    cooling the boss to cause the boss to contract to decrease the contact surface pressure during the heating of the press-fitted portion.

3. The medical apparatus remanufacturing method according to claim 1, wherein
    one of the boss and the boss hole includes a surface portion that contacts with another of the boss and the boss hole in the assembled state, and
    the heating of the press-fitted portion thermally deforms the surface portion to decrease the contact surface pressure.

4. The medical apparatus remanufacturing method according to claim 1, wherein the press-fitted portion is heated at a temperature lower than a heat resistant temperature of the second housing.

5. The medical apparatus remanufacturing method according to claim 1, further comprising:
    reassembling the first housing and the second housing to each other after the disassembling; and
    then performing a sterilization treatment including sending a sterilizing gas to the boss hole through a flow channel that allows passage of fluid and is provided between an outer surface of the boss and an inner surface of the boss hole,
    wherein the flow channel extends in a longitudinal direction running from a proximal end of the boss to a distal end of the boss.

6. A medical apparatus remanufacturing method comprising:
    disassembling a housing including a first housing and a second housing, the first housing including a boss that is press-fitted to a boss hole of a press-fitted portion of the second housing in an assembled state in which the first housing and the second housing are assembled to each other, the disassembling including:
        heating at least one of the boss and the press-fitted portion so as to thermally deform a portion of one of the boss and the boss hole that is in contact with another of the boss and the boss hole in the assembled state to decrease a contact surface pressure between the boss and the boss hole, wherein the at least one of boss and a press-fitted portion is heated to a temperature equal to or greater than a heat resistant temperature of the portion of one of the boss and the boss hole that is in contact with another of the boss and the boss hole in the assembled state; and
        removing the boss from the boss hole to release the assembled state.

7. The medical apparatus remanufacturing method according to claim 6, wherein the portion of one of the boss and the boss bole that is in contact with another of the boss and the boss hole in the assembled state is disposed on one of an outer surface of the boss and an inner surface of the boss hole.

8. The medical apparatus remanufacturing method according to claim 6, further comprising:
reassembling the first housing and the second housing to each other after the disassembling; and
then performing a sterilization treatment including sending a sterilizing gas to the boss hole through a flow channel that allows passage of fluid and is provided between an outer surface of the boss and an inner surface of the boss hole,
wherein the flow channel extends in a longitudinal direction running from a proximal end of the boss to a distal end of the boss.

9. The medical apparatus remanufacturing method according to claim 6, wherein
the heating of at least one of the boss and the press-fitted portion increases a strain rate in creep deformation in at least one of the boss and the boss hole to decrease the contact surface pressure.

10. The medical apparatus remanufacturing method according to claim 9, wherein
the at least one of the boss and the press-fitted portion is heated through a hole extending inward from an outer surface of at least one of the first housing and the second housing.

11. The medical apparatus remanufacturing method according to claim 6, wherein the boss includes a cutout and the portion of one of the boss and the boss hole that is in contact with another of the boss and the boss hole in the assembled state is embedded in the cutout.

12. The medical apparatus remanufacturing method according to claim 11, wherein the cutout extends from a distal end of the boss toward a proximal end side of the boss to divide the boss into two members in a radial direction of the boss.

13. A medical apparatus remanufacturing method comprising:
disassembling a housing including a first housing and a second housing, the first housing including a boss that is press-fitted to a boss hole of a press-fitted portion of the second housing in an assembled state in which the first housing and the second housing are assembled to each other, the disassembling including:
removing the boss from the boss hole to release the assembled state;
then reassembling the first housing and the second housing to each other; and
then performing a sterilization treatment including sending a sterilizing gas to the boss hole through a flow channel that is configured to allow passage of fluid and is formed between an outer surface of the boss and an inner surface of the boss hole,
wherein the flow channel extends in a longitudinal direction running from a proximal end of the boss to a distal end of the boss.

14. The medical apparatus remanufacturing method according to claim 13, wherein the disassembling further includes:
changing a temperature of at least one of the boss and the press-fitted portion to decrease a contact surface pressure between the boss and the boss hole.

15. The medical apparatus remanufacturing method according to claim 14, wherein
the changing of the temperature further includes cooling the boss to cause the boss to contract to decrease the contact surface pressure.

16. The medical apparatus remanufacturing method according to claim 14, wherein
the changing of the temperature includes heating the press-fitted portion to thermally expand the boss hole to decrease the contact surface pressure.

17. The medical apparatus remanufacturing method according to claim 16, wherein
the press-fitted portion has a thermal expansion coefficient higher than a thermal expansion coefficient of the boss.

18. The medical apparatus remanufacturing method according to claim 14, wherein
the changing of the temperature includes heating at least one of the boss and the press-fitted portion to increase a strain rate in creep deformation in at least one of the boss and the boss hole to decrease the contact surface pressure.

19. The medical apparatus remanufacturing method according to claim 18, wherein
the at least one of the boss and the press-fitted portion is heated through a hole extending inward from an outer surface of at least one of the first housing and the second housing.

\* \* \* \* \*